US00PP33707P2

(12) United States Plant Patent
Van Swieten

(10) Patent No.: US PP33,707 P2
(45) Date of Patent: Nov. 30, 2021

(54) *PHALAENOPSIS* ORCHID PLANT NAMED 'PHALILUG'

(50) Latin Name: ***Phalaenopsis* hybrid**
Varietal Denomination: PHALILUG

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,447

(22) Filed: Jul. 1, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALILUG', particularly characterized by light yellow-green, flecked flowers with dark red lips, strong curvature of the lateral lobe of the lip, apical lobe of the lip with a small bump and ridge, and is propagated by meristem tissue culture, is disclosed.

3 Drawing Sheets

Genus and species: *Phalaenopsis* hybrid.
Variety denomination: 'PHALILUG'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALILUG'.

The new *Phalaenopsis* plant is a product of a planned breeding program conducted by the inventor in Bleiswijk, the Netherlands. The objective of this breeding program was to create a new *Phalaenopsis* plant with light yellow-green, flecked flowers with dark red lips, suitable for potted plant production.

The new *Phalaenopsis* plant 'PHALILUG' is a result of cross-pollination made by the inventor in February 2012 in Bleiswijk, the Netherlands, of the proprietary female, or seed parent, *Phalaenopsis* hybrid '01-4155' (unpatented) with the proprietary male, or pollen parent, *Phalaenopsis* hybrid '01-3358' (unpatented).

The new *Phalaenopsis* was selected by the inventor as a single plant within the progeny of the stated cross-pollination in a controlled greenhouse in Bleiswijk, the Netherlands, in January 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 20, 2019 (Application no. 2019/2324), by Applicant who obtained the subject matter disclosed directly from the inventor. 'PHALILUG' has not been made publicly available or sold anywhere in the world prior to the effective filing date of this application with the exception of sales or disclosures made one year or less before the effective filing date of this claimed invention by Applicant who obtained 'PHALILUG' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALILUG' as a new and distinct variety of *Phalaenopsis* plant:

1) Light yellow-green, flecked flowers with dark red lips (intensity and number of flecks depend on the temperature during growing period);
2) Curvature of lateral lobe of the lip is strong; and
3) Apical lobe of the lip has a small bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in May 2021. Colors in the photographs may differ from the color values cited in the detailed botanical description, which accurately describe the actual colors of the new variety.

DESCRIPTION OF THE NEW VARIETY

Figure 1:
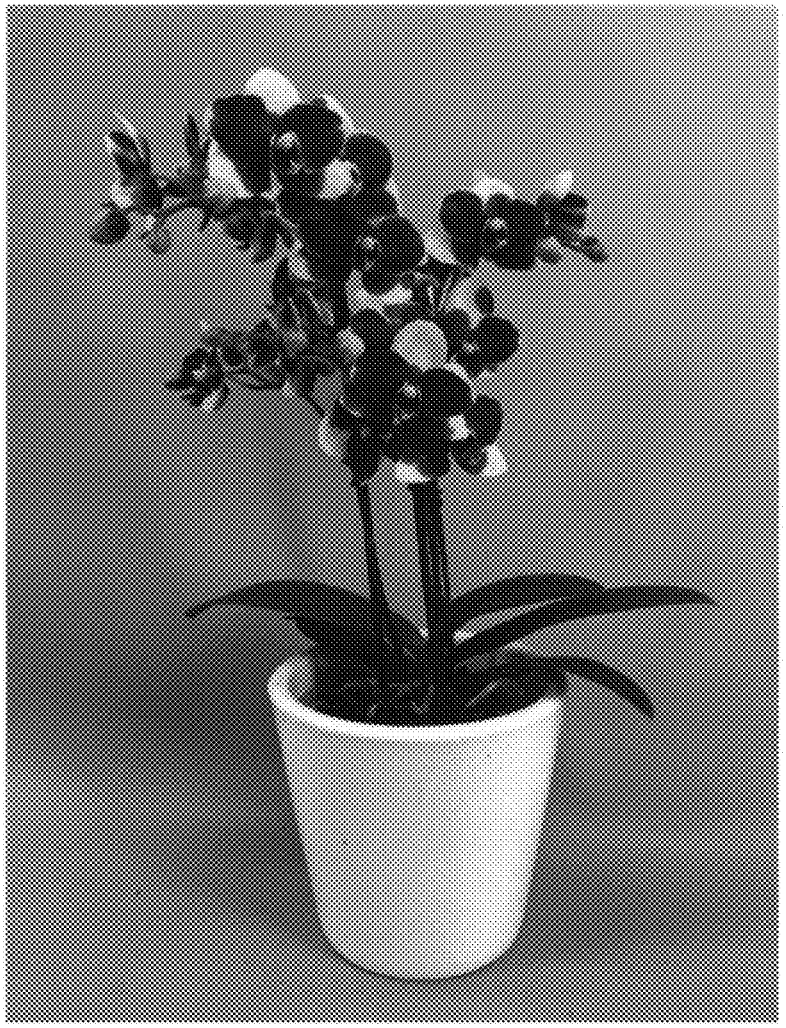
FIG. 1 shows the overall plant habit, including blooms, buds, and foliage of 'PHALILUG'.
Figure 2:
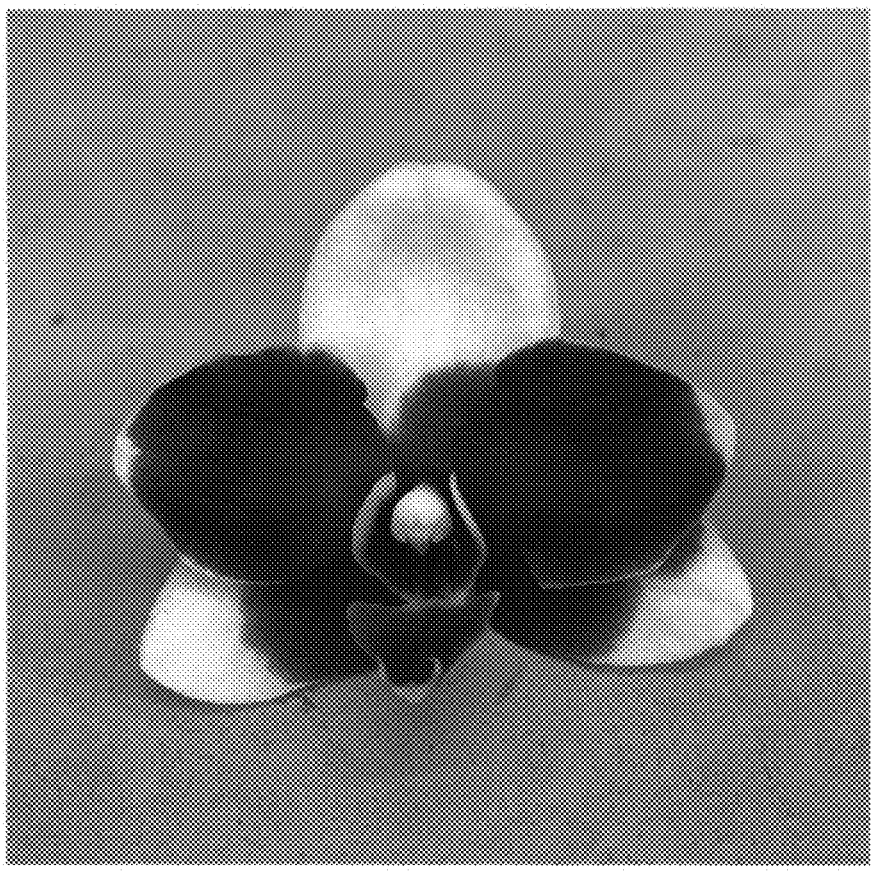
FIG. 2 shows a close-up of a flower of 'PHALILUG'.
Figure 3:
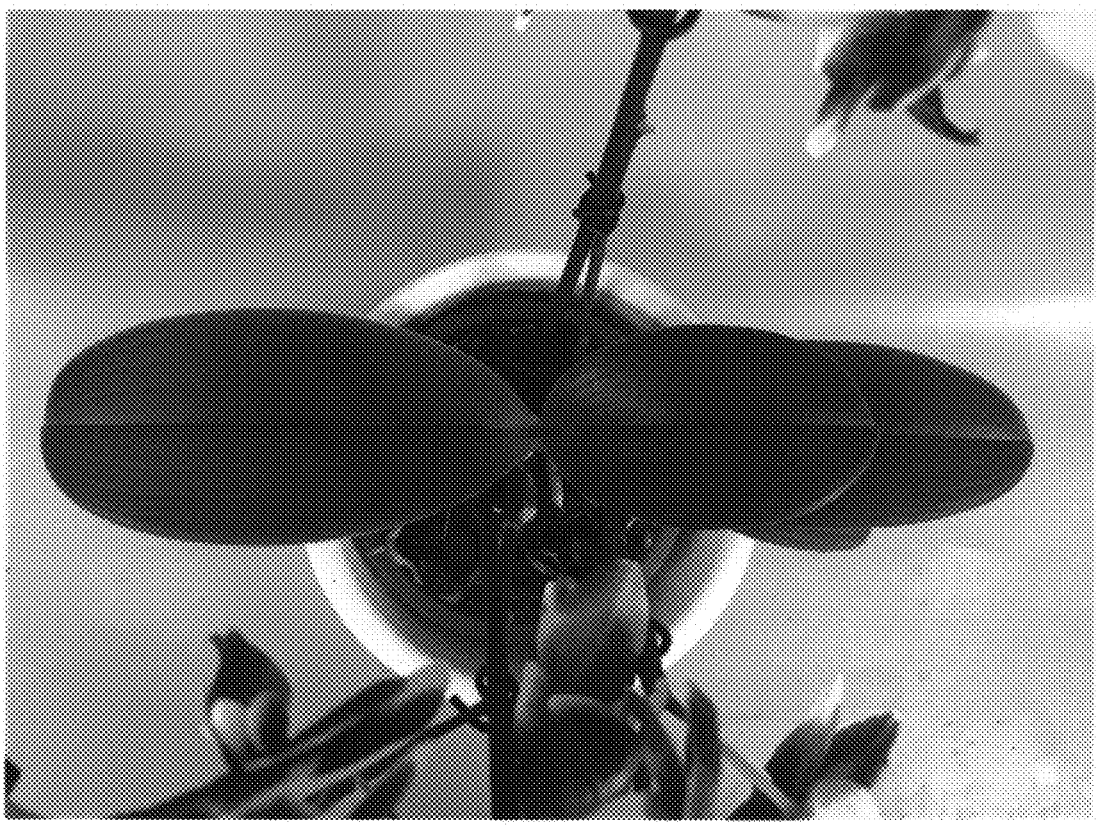
FIG. 3 shows an overhead view of the leaves of 'PHALILUG'.

The following detailed description sets forth the distinctive characteristics of 'PHALILUG'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALILUG'.

Parentage:

*Female parent.*—*Phalaenopsis* cultivar '01-4155' (unpatented).

*Male parent.*—*Phalaenopsis* cultivar '01-3358' (unpatented).

Propagation:

*Type.*—Meristem tissue culture.

Roots:

*Root description.*—Greyed-green (a color in between RHS 190B and RHS 190C) colored roots with branching lateral roots having yellow-green (RHS 145C) colored root tips.

Plant:

*Crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme and panicle inflorescence.

*Height* (*from soil level to top of inflorescence*).—Approximately 27.0 cm to 32.0 cm.

*Width* (*measured from leaf tips*).—About 22.0 cm to 27.0 cm.

*Vigor.*—Strong.

Leaves:

*Mature leaves.*—Quantity per plant 6 to 8 leaves are produced before flowering. Length (fully expanded): 13.0 cm to 15.0 cm. Width: 6.0 cm to 7.0 cm. Position of the broadest part of the leaf: At the middle. Shape: Oblong. Base shape: Slightly to moderately elongated. Apex: Unequal obtuse. Leaf blade angle with the petiole (measured from the horizontal position): Between 20 degrees and 30 degrees. Leaf margin: Entire. Color: Upper surface: RHS 147A. Lower surface: RHS 147B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 147B.

Peduncle:

*Quantity per plant.*—1 to 3.

*Number of flowers per peduncle.*—10 to 15.

*Length.*—27.0 cm to 32.0 cm.

*Diameter.*—3.0 mm to 4.0 mm.

*Strength.*—Strong.

*Aspect.*—Upright to slightly pendent.

*Texture.*—Smooth.

*Color.*—Green (RHS 146A) with a hint of brown (RHS N200A) at the base.

*Internode length.*—2.5 cm to 3.5 cm.

Inflorescence description:

*Appearance.*—Upright to slightly pendent, raceme and panicle inflorescence with bilaterally symmetrical flowers that open in succession beginning with the lowermost flower.

*Number of inflorescences.*—1 to 3.

*Inflorescence size.*—Height (from base to tip): 140.0 mm to 190.0 mm.

*Flowering time.*—First flowers can be expected 10 to 11 months after planting in a 12-cm pot.

*Flower.*—Height: 45.0 mm to 50.0 mm. Diameter: 50.0 mm to 55.0 mm. Depth of lip: 13.0 mm to 15.0 mm.

*Flower longevity.*—On the plant: 9 to 11 weeks.

*Flower shape.*—Flat.

*Fragrance.*—Absent.

*Flower bud.*—Average size: Medium. Length: 13.0 mm to 15.0 mm. Width: 11.0 mm to 13.0 mm. Shape: Egg shaped. Color: Dark purplish-red flecks (RHS N79C) at the base; yellow-green (RHS N144D) toward the tip.

*Petals.*—Arrangement: Open/free. Shape: Semi-circular. Apex: Obtuse asymmetric. Margin: Moderately undulated. Length (from base to tip): 23.0 mm to 25.0 mm. Width: 22.0 mm to 24.0 mm. Position of the broadest part of the petal: Toward the base. Color (when fully opened): Upper surface: Basic color: Dark red (RHS 187C). Over color: Diluting dark red flecks (RHS 187A); light yellow-green margin and the tip (RHS 154D). Lower surface: Basic color: Dark purplish-red (RHS N79C). Over color: Diluting dark red flecks (RHS 187A); greyish-yellow-green (RHS 195B) at the middle. Number of spots, flecks, and stripes on the petals (upper surface): Very few flecks. Color of spots, flecks, and stripes on the petals (upper surface): RHS 187A. Density of netting of the petals (upper surface): None. Color of the netting (upper surface): Not applicable.

*Dorsal sepal.*—Shape: Elliptic. Apex: Slightly emarginated symmetric. Margin: Entire. Length (from base to tip): 27.0 mm to 29.0 mm. Width: 22.0 mm to 24 0 mm. Position of the broadest part of the dorsal sepals: At the middle. Color (when fully opened): Upper surface: Basic color: Light yellow-green (RHS 154D). Over color: Dark purple-red fleck (a color in between RHS N79C and RHS 187C) at the base. Lower surface: Basic color: Light greenish-yellow (RHS 1D). Over color: Diluting dark purple-red fleck (a color in between RHS N79C and RHS 187B) at the base; touch of light greenish-yellow (RHS 6D) at the middle. Number of spots, flecks, and stripes on the dorsal sepals (upper surface): Very few flecks. Color of spots, flecks, and stripes on the dorsal sepals (upper surface): A color in between RHS N79C and RHS 187C. Density of netting of the dorsal sepals (upper surface): None. Color of the netting: Not applicable.

*Lateral sepals.*—Shape: Ovate. Apex: Obtuse symmetric. Margin: Entire. Length (from base to tip): 28.0 mm to 30.0 mm. Width: 18.0 mm to 20.0 mm. Position of the broadest part of the lateral sepals: At the base. Color (when fully opened): Upper surface: Basic color: Light greenish-yellow (RHS 1C). Over color: Dark purplish-red (RHS N79C) and dark red flecks (RHS 187A) at the base. Lower surface: Basic color: Light greenish-yellow (RHS 1D). Over color: Diluting dark red fleck (RHS 187B) at the base and toward the middle becomes lighter (RHS N79C); light greenish-yellow midvein (RHS 6D) toward the tip. Number of spots, flecks, and stripes on the lateral sepals (upper surface): Very few flecks. Color of spots, flecks, and stripes on the lateral sepals (upper surface): RHS 187A. Density of netting of the lateral sepals (upper surface): None. Color of the netting (upper surface): Not applicable.

*Labellum* (*lip*).—Whiskers: Present. Length of whiskers: 2.0 mm to 4.0 mm. Color of whiskers: Purplish-red (RHS 187D) at the base with pinkish-white tips (RHS N155B). Pubescence on the lip: Absent.

*Lateral lobe.*—Shape: Type IV (as described in the International Union for the Protection of New Varieties of Plants (UPOV) Test Guidelines for *Phalaenopsis*); weakly spatulate. Margin: Entire. Length: 11.0 mm to 13.0 mm. Width: 7.0 mm to 9.0 mm. Color: Upper surface: Dark red (a color in between RHS 187B and RHS 187C) at the base with few darker red flecks (RHS 187A); greenish-yellow (RHS 6A) at margin on one side toward the tip; white (RHS NN155C) toward the other side. Lower surface: Yellowish-grey (RHS 156B) at the base; diluting dark red (RHS 187B); greenish-yellow (RHS 6B) at margin on one side toward the tip; white (RHS NN155C) toward the other side. Number of spots, flecks, and stripes on the lateral lobe: Few flecks. Color of spots, flecks, and stripes on the lateral lobe: RHS 187A. Density of netting of the lateral lobe: None. Color of the netting: Not applicable.

*Apical lobe.*—Shape: Rhombic. Margin: Entire. Length: 14.0 mm to 16.0 mm. Width: 13.0 mm to 15.0 mm. Color: Upper surface: Yellow (RHS 9A) at the base; dark red (a color in between RHS 187B and RHS 187C) with few darker red flecks (RHS 187A) toward whiskers. Lower surface: Yellow (RHS 9B) at the base; dark red (RHS 187C) toward margins on both sides; white (RHS NN155C) at the middle toward whiskers. Number of spots, flecks, and stripes on the apical lobe: Few flecks. Color of spots, flecks, and stripes on the apical lobe: RHS 187A. Density of netting of the apical lobe: None. Color of the netting: Not applicable. Bump and ridge: Present; small.

*Callus.*—Average size: Small. Height: 3.0 mm to 4.0 mm. Length: 2.0 mm to 3.0 mm. Width: 2.0 mm to 3.0 mm. Color: Dark red (RHS 187A) and greenish-white (RHS 157D) on sides.

Reproductive organs:

*Column.*—Length: 8.0 mm to 10.0 mm. Diameter: 3.5 mm to 4.2 mm. Color: Touch of dark purplish-red (RHS N79C) at the base and white (RHS NN155C) toward the top.

*Pollinia.*—Quantity: 2. Diameter: 0.7 mm to 0.9 mm. Color: Orange-yellow (RHS 23A).

*Ovary.*—Length: 9.0 mm to 11.0 mm. Diameter: 1.5 mm to 1.7 mm.

*Pedicel.*—Length: 26.0 mm to 28.0 mm. Diameter: 1.7 mm to 1.9 mm. Color: Touch of dark purplish-red (RHS N79B) at the base; light yellow-green (RHS 145B) and lighter yellow-green (RHS 145D) toward the flower. Texture: Smooth.

Disease, Pest, and Stress Resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALILUG' differs from the female parent plant '01-4155' (unpatented) in that 'PHALILUG' has petals with a main color of dark red, strong curvature of the lateral lobe of the lip, and whiskers, whereas '01-4155' has petals with a main color of greenish-yellow, weak curvature of the lateral lobe of the lip, and no whiskers.

'PHALILUG' differs from the male parent plant '01-3358' (unpatented) in that 'PHALILUG' has petals with a main color of dark red and a flecked pattern, and rhombic apical lobes, whereas '01-3358' has petals with a main color of purplish-pink and a striped pattern, and ovate apical lobes.

'PHALILUG' is most similar to the commercial *Phalaenopsis* plants named 'PHALIDDIK' (U.S. Plant Pat. No. 33,523) and 'PHALUSYL' (U.S. Plant Pat. No. 31,166). 'PHALILUG' differs from the commercial variety 'PHALIDDIK' in that 'PHALILUG' has rhombic apical lobes with a main color of dark red, and strong curvature of the lateral lobe of the lip, whereas 'PHALIDDIK' has ovate apical lobes with a main color of white, and medium curvature of the lateral lobe of the lip.

'PHALILUG' differs from the commercial variety 'PHALUSYL' in that 'PHALILUG' has rhombic apical lobes, strong curvature of the lateral lobe of the lip, and whiskers, whereas 'PHALUSYL' has obtrullate apical lobes, weak curvature of the lateral lobe of the lip, and no whiskers.

I claim:

1. A new and distinct variety of *Phalaenopsis* plant named 'PHALILUG', substantially as described and illustrated herein.

* * * * *